United States Patent
Hotta et al.

(10) Patent No.: US 9,523,694 B2
(45) Date of Patent: Dec. 20, 2016

(54) IDENTIFICATION OF ATYPICAL ANTIBODIES IN HUMAN BLOOD AND BLOOD PRODUCTS

(71) Applicant: GRIFOLS, S.A., Barcelona (ES)

(72) Inventors: Joann Hotta, Raleigh, NC (US); Clark Zervos, Raleigh, NC (US)

(73) Assignee: GRIFOLS, S.A., Barcelona (ES)

( * ) Notice: Subject to any disclaimer, the term of this patent is extended or adjusted under 35 U.S.C. 154(b) by 0 days.

(21) Appl. No.: 14/367,883

(22) PCT Filed: Nov. 22, 2012

(86) PCT No.: PCT/IB2012/056629
§ 371 (c)(1),
(2) Date: Jun. 20, 2014

(87) PCT Pub. No.: WO2013/093671
PCT Pub. Date: Jun. 27, 2013

(65) Prior Publication Data
US 2015/0132773 A1    May 14, 2015

Related U.S. Application Data

(60) Provisional application No. 61/578,290, filed on Dec. 21, 2011.

(51) Int. Cl.
*G01N 33/53* (2006.01)
*G01N 33/68* (2006.01)
*G01N 33/564* (2006.01)
*G01N 33/80* (2006.01)

(52) U.S. Cl.
CPC ........ *G01N 33/6854* (2013.01); *G01N 33/564* (2013.01); *G01N 33/80* (2013.01); *G01N 2333/4713* (2013.01)

(58) Field of Classification Search
CPC .. G01N 33/6854; G01N 33/564; G01N 33/80; G01N 33/53; G01N 2333/4713
See application file for complete search history.

(56) References Cited

U.S. PATENT DOCUMENTS

| 4,472,357 A * | 9/1984 | Levy et al. .................... 604/403 |
| 2007/0172899 A1 | 7/2007 | Graham et al. |
| 2010/0178656 A1 * | 7/2010 | Buffiere et al. ................ 435/7.1 |

FOREIGN PATENT DOCUMENTS

| CN | 101711363 A | 5/2010 |
| CN | 101346630 A | 7/2013 |
| WO | 2008033164 A1 | 3/2008 |

OTHER PUBLICATIONS

Harmening, Modern Blood Banking and Transfusion Practices, Third Edition, 1994, Chapter 10, p. 219.*
Office Action dated Apr. 3, 2015 for CN Application No. 201280046051.7.
International Search Report dated Mar. 28, 2013 for PCT/IB2012/056629.

* cited by examiner

*Primary Examiner* — Gary W Counts
(74) *Attorney, Agent, or Firm* — Knobbe, Martens, Olson & Bear, LLP

(57) ABSTRACT

A method identifies atypical antibodies in blood or blood product manufacturing processes that may produce false positives in quality control testing on intermediate or final products.

5 Claims, 15 Drawing Sheets

FIG. 1
A Donor X – Positive Agglutination
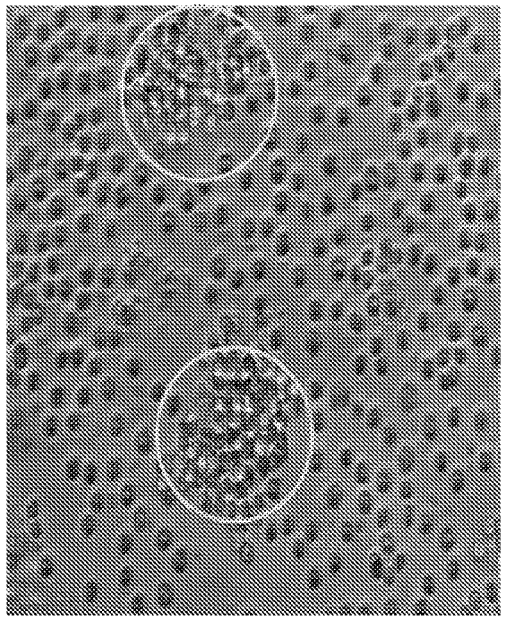
B Control – Negative Agglutination
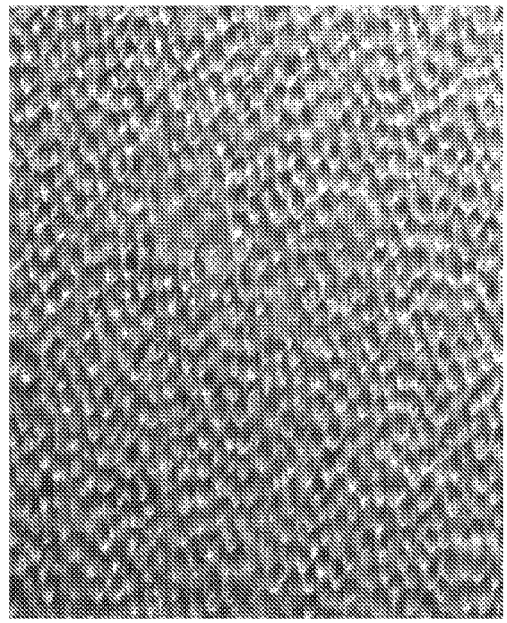
C Donor X – Positive Agglutination
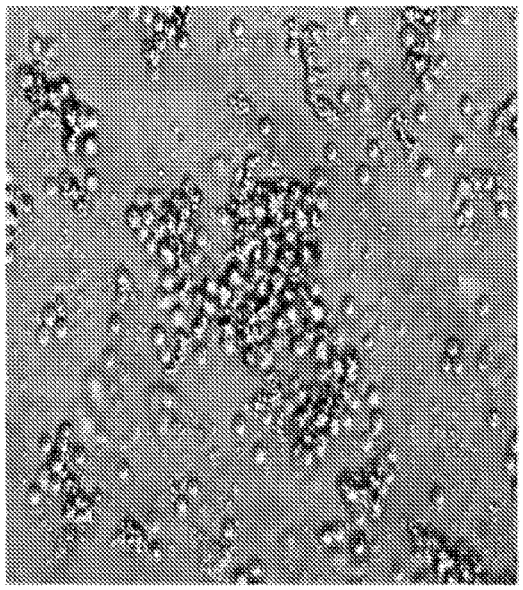
D Control – Negative Agglutination
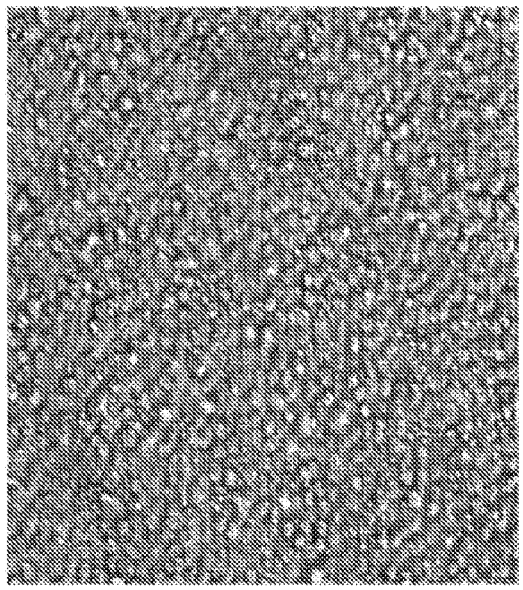

FIG.2
A Donor X – Negative Agglutination
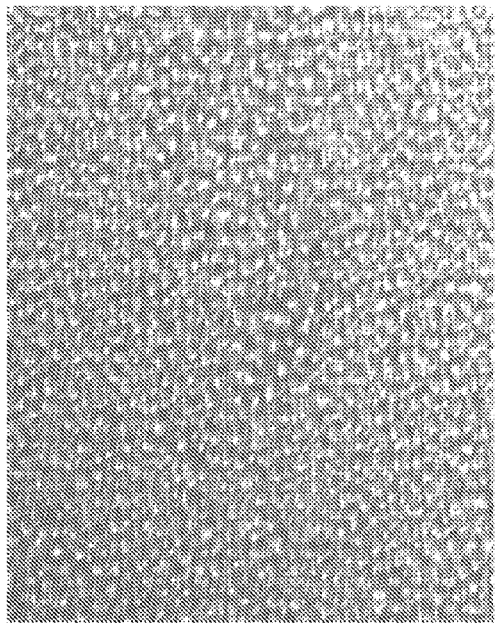
B Control – Negative Agglutination
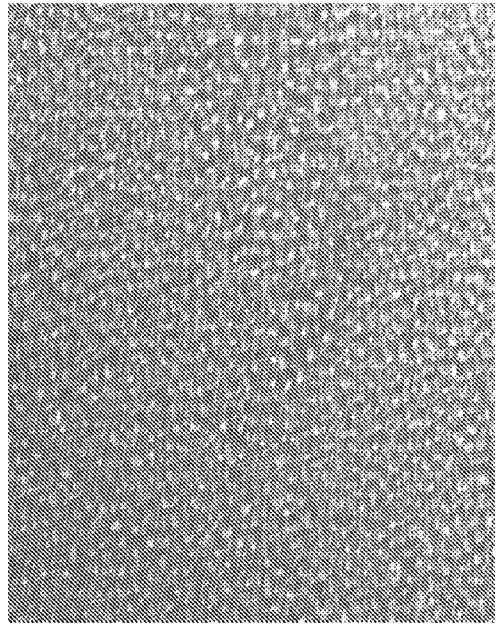
C Donor X – Negative Agglutination
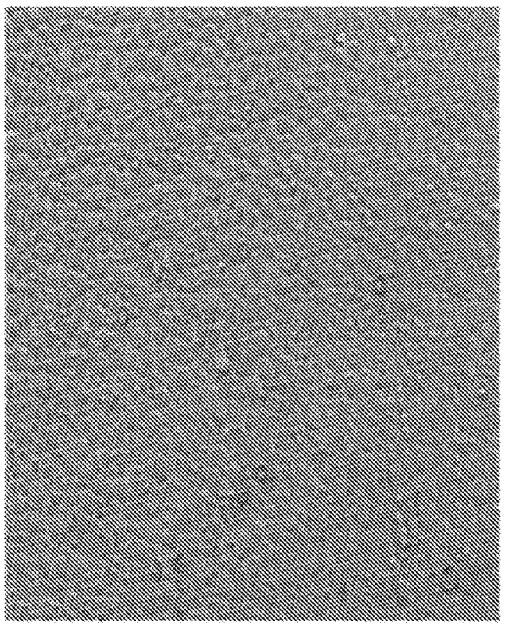
D Control – Negative Agglutination
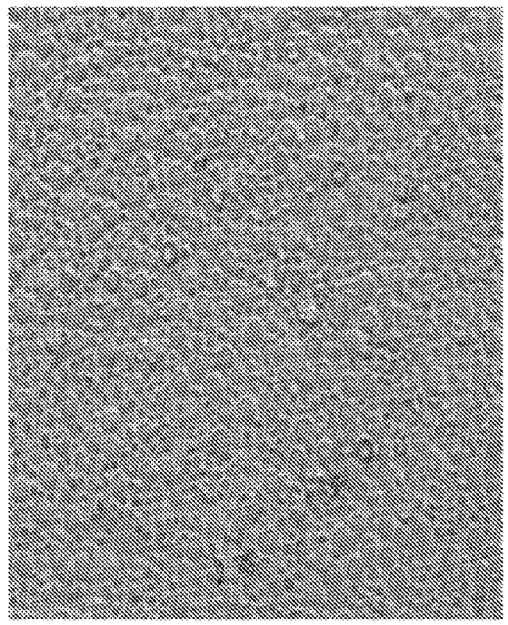

FIG. 3
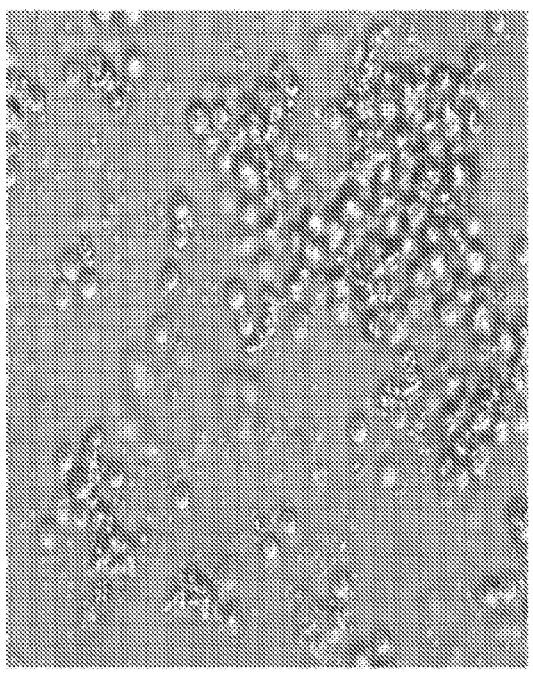
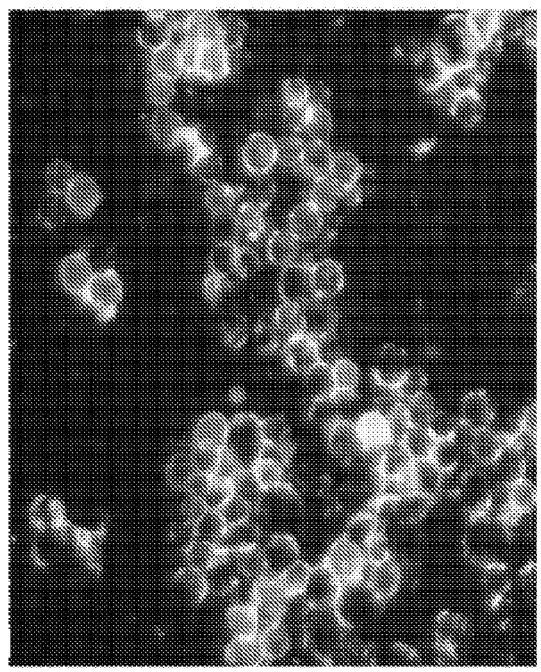

FIG. 4
A Donor X – Strong Fluorescence 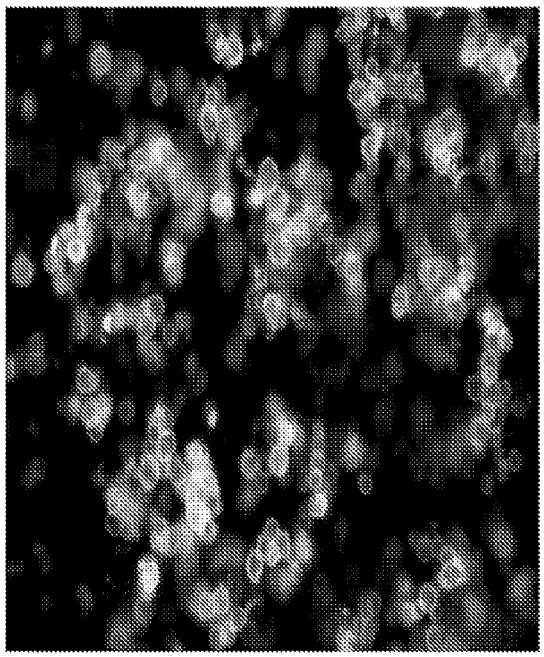
B Control – Weak Fluorescence 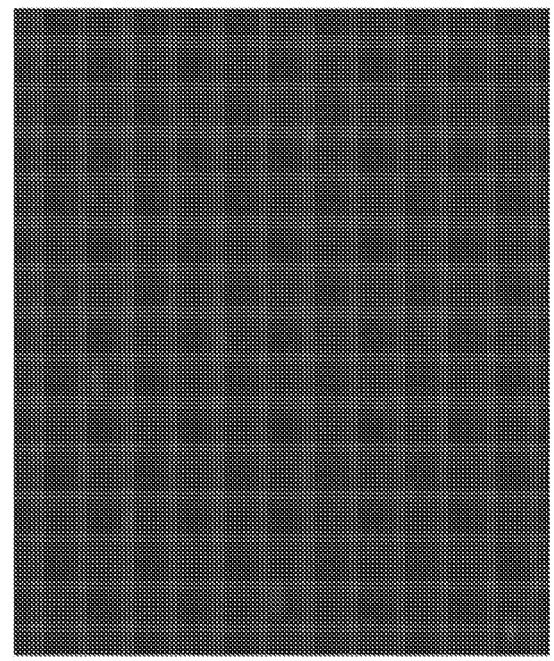

FIG. 5
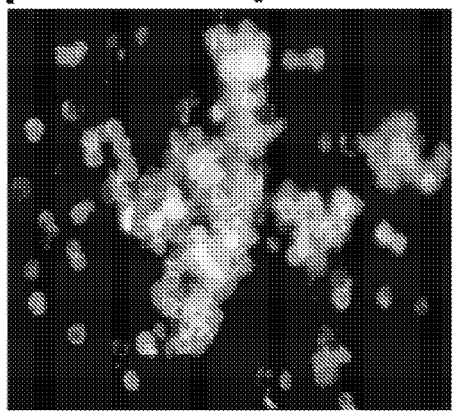
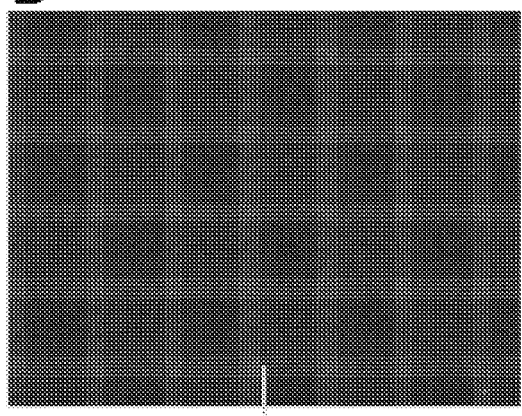
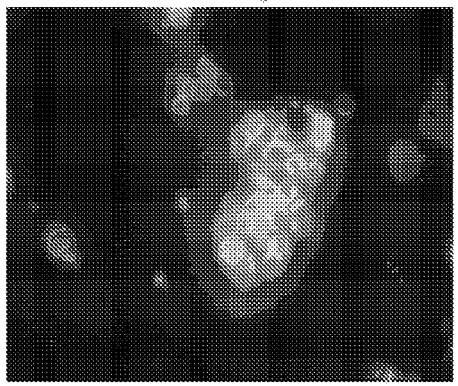
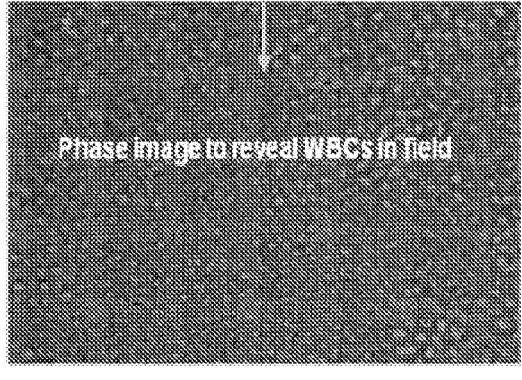

FIG. 6
A Donor X – Weak Fluorescence
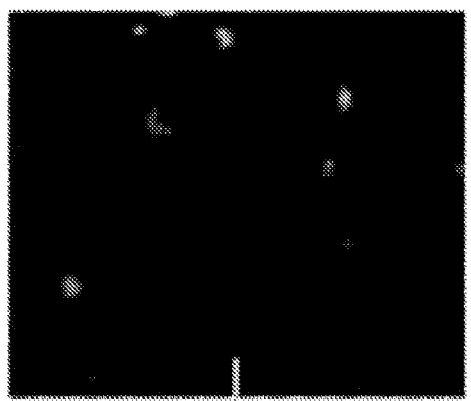
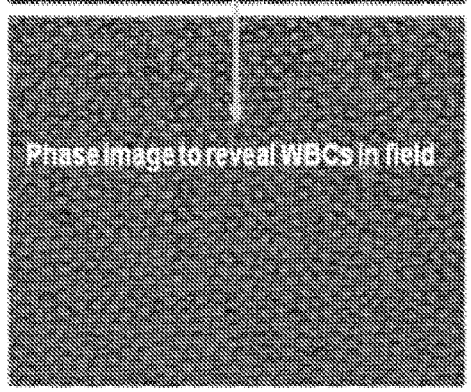
B Control – Weak Fluorescence
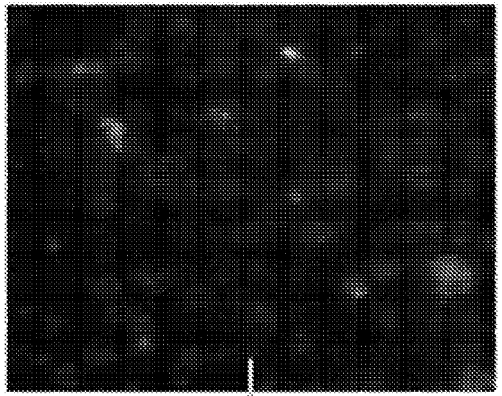
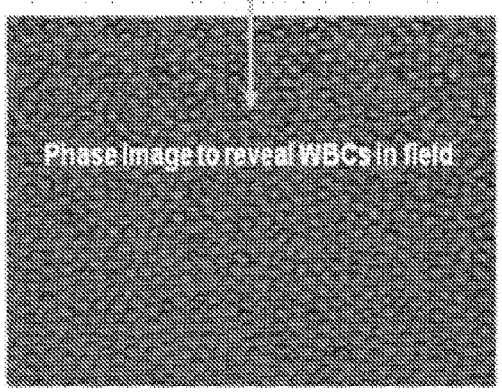

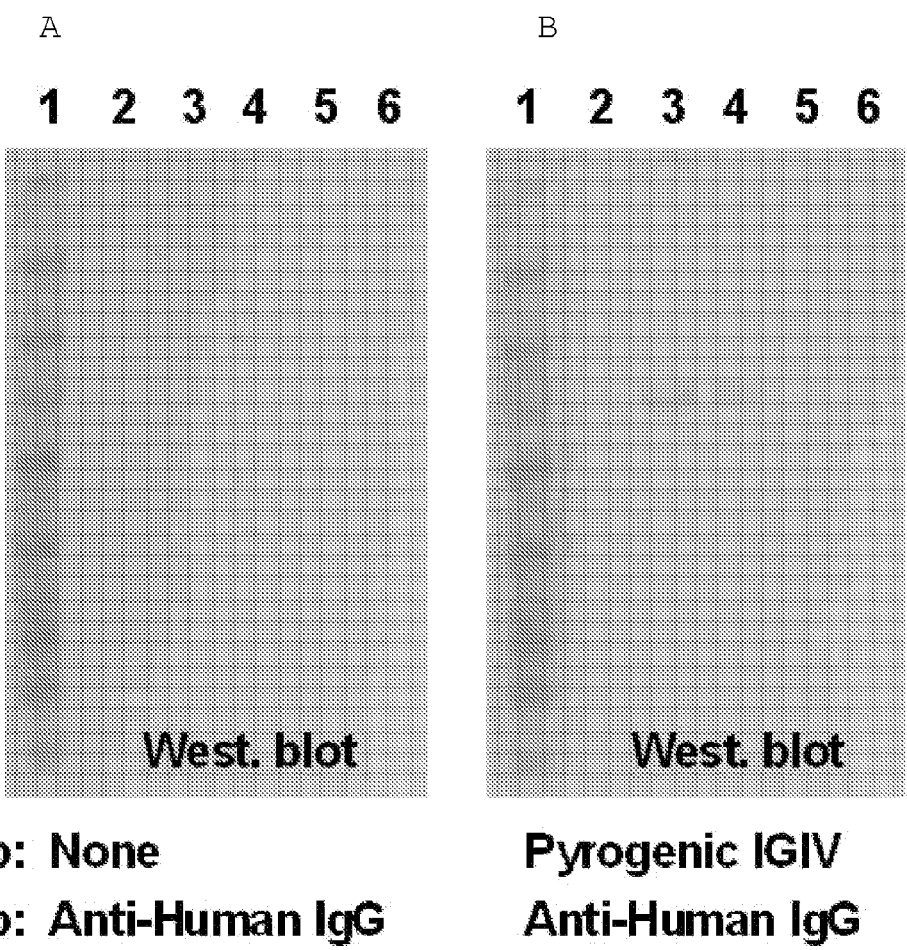

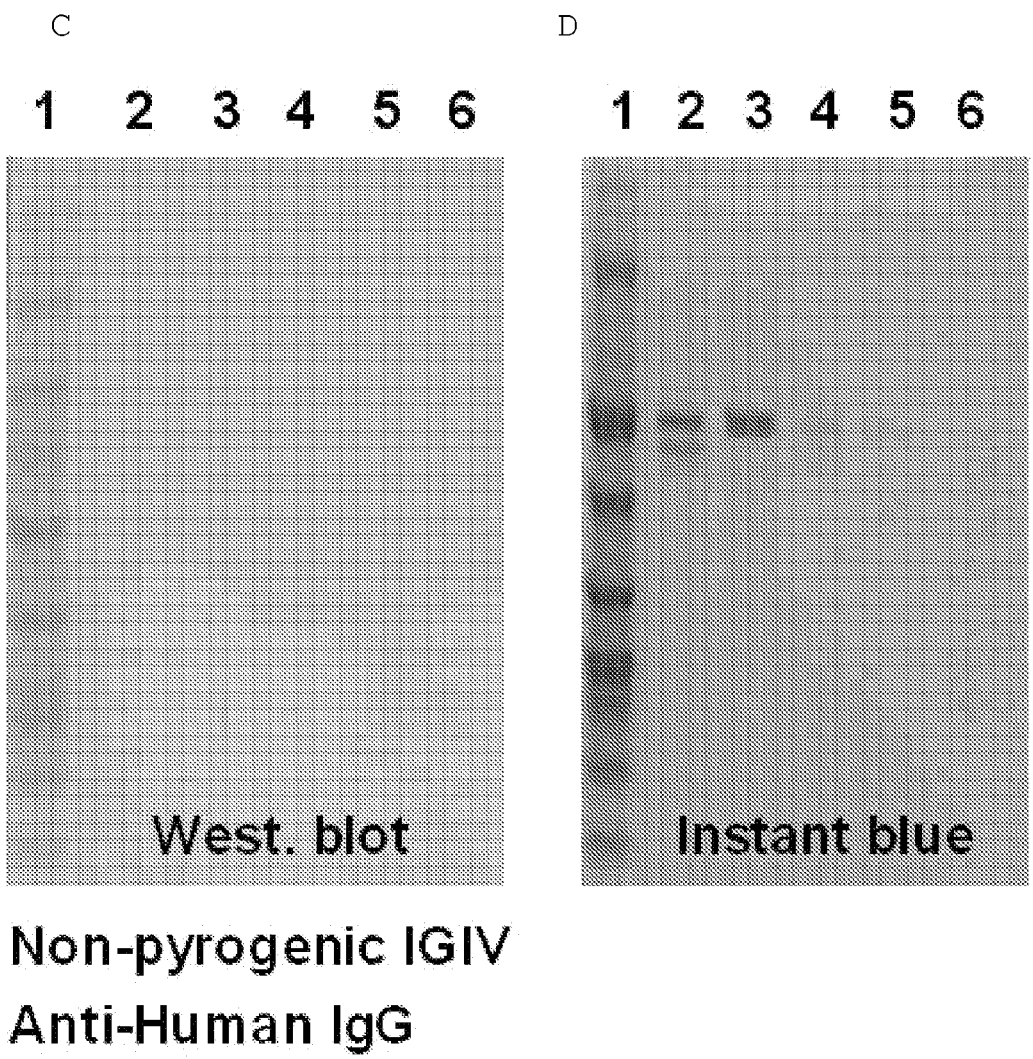

US 9,523,694 B2

IDENTIFICATION OF ATYPICAL ANTIBODIES IN HUMAN BLOOD AND BLOOD PRODUCTS

CROSS REFERENCE TO RELATED APPLICATIONS

This application is the U.S. National Phase of International Application No. PCT/IB2012/056629, filed Nov. 22, 2012, designating the U.S. and published as WO 2013/093671 on Jun. 27, 2013 which claims the benefit of U.S. Provisional Patent Application No. 61/578,290, filed Dec. 21, 2011.

TECHNICAL FIELD

Described herein are methods for identifying atypical antibodies in blood and blood products.

BACKGROUND

Natural human antibodies have been identified that cause pyrogenic responses during USP pyrogen tests. Some human donors naturally produce these "atypical antibodies," perhaps resulting from exposure to rabbits, rodents, or paracitic insects preying upon such host animals (i.e., fleas). The atypical antibodies are anomalous and uncommon, but are not harmful to humans. Atypical antibodies can cross-react with rabbit white blood cell antigens and cause a pyrogenic response during rabbit pyrogen tests. The pyrogenic response is, however, a "false positive" result because other methods, such as the limulus amoebocyte lysate assays (LAL), showed that suspect plasma samples giving pyrogenic responses in the rabbit assay do not contain endotoxins. In addition, the results of in vitro pyrogen tests (aka monocyte activation tests) indicate the absence of non-endotoxin pyrogens. Accordingly, atypical antibodies in human blood or plasma cause erroneous rabbit pyrogen test results and may result in the disposal of individual or pooled blood or plasma that falsely tests positive as "pyrogenic."

The methods described herein permit the identification of blood or plasma samples containing atypical antibodies that result in false positives in pyrogen assays. This method is advantageous because atypical antibody-containing samples can be eliminated before pooling with other blood or plasma and contaminating the pool. Accordingly, the method reduces manufacturing cost by preventing the unnecessary contamination of blood or plasma pools with samples that appear "pyrogenic" owing to the presence of atypical antibodies. High throughput testing methods described herein permit identification of suspect falsely positive samples. Such samples can be discarded prior to pooling with other samples and prevent tainting the pool with atypical antibodies.

SUMMARY

Described herein are methods for identifying atypical antibodies in blood and blood products.

One aspect described herein is method for identifying atypical reactive antibodies in a blood products manufacturing process, the method comprising: (a) obtaining a sample of blood or plasma; (b) testing the sample and a control using any one or more of cellular agglutination, fluorescence microscopy, immunoprecipitation, immunodiffusion, immunofluorescence, ELISA, flow cytometry, FACS, or Western blotting; (c) comparing the sample and control testing results; (d) determining whether the sample contains reactive atypical antibodies; and; (e) interdicting a blood or plasma unit that was the source of the sample if the sample contains reactive atypical antibodies.

Another aspect described herein is a method for identifying atypical reactive antibodies in a blood products manufacturing process, the method comprising: (a) obtaining a sample of blood or plasma; (b) testing the sample and a control using a cellular agglutination assay; (c) comparing the sample and control testing results; (d) determining whether the sample contains reactive atypical antibodies; and; (e) interdicting a blood or plasma unit that was the source of the sample if the sample contains reactive atypical antibodies.

Another aspect described herein is a method for identifying atypical reactive antibodies in a blood products manufacturing process, the method comprising: (a) obtaining a sample of blood or plasma; (b) testing the sample and a control using flow cytometry; (c) comparing the sample and control testing results; (d) determining whether the sample contains reactive atypical antibodies; and; (e) interdicting a blood or plasma unit that was the source of the sample if the sample contains reactive atypical antibodies.

Another aspect described herein is a method for identifying atypical reactive antibodies in a blooda plasma products manufacturing process, the method comprising: (a) obtaining a sample of blood or plasma; (b) testing the sample and a control using Western blotting; (c) comparing the sample and control testing results; (d) determining whether the sample contains reactive atypical antibodies; and; (e) interdicting a blood or plasma unit that was the source of the sample if the sample contains reactive atypical antibodies.

Another aspect described herein is a method for evaluating potential false positive pyrogen test results in a blood products manufacturing process, the method comprising: (a) obtaining a sample of blood or blood product; (b) testing the sample and a control using fluorescence microscopy, immunoprecipitation, immunodiffusion, immunofluorescence, ELISA, flow cytometry, FACS, or Western blotting; (c) testing the sample and a control using the Limulus Amebocyte Lysate (LAL) or similar assay; (d) comparing the sample and control testing results in both assays; (e) evaluating whether the sample gave a false positive pyrogen test result; and (f) interdicting a blood or plasma unit that was the source of the sample if the sample contains reactive atypical antibodies.

BRIEF DESCRIPTION OF THE DRAWINGS

FIG. 1: Microscopy of Rabbit WBC Agglutination Assays. Donor X and control plasma were incubated with rabbit WBCs and then viewed using microscopy. Light (A, B) and phase contrast (C, D) photomicrographs of rabbit white blood cells incubated with Donor X plasma (A, C) or control plasma (B, D). Agglutination was observed with the Donor X plasma (A, C), but not with the plasma control (B, D).

FIG. 2: Microscopy of Human WBC Agglutination Assays. Donor X and control plasma were incubated with human WBCs and then viewed using microscopy. Light (A, B) and phase contrast (C, D) photomicrographs of human white blood cells incubated with Donor X plasma (A, C) or a control plasma (B, D). No agglutination was observed with the Donor X plasma (A, C) or the plasma control (B, D).

FIG. 3: Phase Contrast and Fluorescence Microscopy of Donor X Rabbit WBC Agglutination. Donor X and control plasma were incubated with rabbit WBCs, reacted with fluorescein-fabled anti-human IgG, and then viewed using phase contrast or fluorescence microscopy. Panel (A) shows a phase contrast photomicrograph of rabbit WBCs incubated with Donor X plasma. Panel (B) shows a fluorescent photomicrograph of rabbit WBCs incubated with Donor X plasma and then treated with fluorescein-labeled anti-human IgG. Strong fluorescence was observed in the agglutinated cell clusters indicating human IgG from Donor X plasma was responsible for cellular agglutination.

FIG. 4: Fluorescence Microscopy of Rabbit WBC Agglutination Assays. Donor X and control plasma were incubated with rabbit WBCs and then reacted with fluorescein-labeled anti-human IgG. Panel (A) shows positive fluorescence of rabbit WBCs. Panel (B) shows the results with control plasma.

FIG. 5: Fluorescence Microscopy of Rabbit WBC Agglutination Assays. Donor X and control plasma were incubated with rabbit WBCs, reacted with fluorescein-labeled anti-human IgG, and then viewed using fluorescence microscopy. Panel (A) shows positive fluorescence of rabbit WBCs incubated with fluorescein-labeled anti-human IgG and a 40× image of the agglutinated cells (bottom panel). These results indicate that Donor X's plasma contains IgGs reactive with rabbit WBC cell-surface antigens. Panel (B) shows the weak fluorescence observed with the control plasma and a phase contrast photomicrograph of the rabbit WBCs showing no agglutination (bottom panel).

FIG. 6: Fluorescence Microscopy of Human WBC Agglutination
Assays. Donor X and control plasma were incubated with human WBCs, reacted with fluorescein-labeled anti-human IgG, and then viewed using fluorescence microscopy. Neither (A, Donor X) nor (B, control plasma) have strong fluorescence or agglutination (bottom panels) indicating that Donor X's plasma contains IgGs not reactive to human WBC cell-surface antigens.

FIG. 10: Electrophoresis and Western Blotting Analysis of Samples of Pyrogenic IVIG-C Containing Donor X Plasma Isolates. Lane 1: MW markers; Lane 2: Fetal Bovine Serum; Lane 3: Rabbit Serum; Lane 4: Rabbit Serum, diluted 1:5; Lane 5: Rabbit Serum, diluted 1:10; Lane 6: Rabbit Serum, diluted 1:50. (A) Western blot control (no primary antibody) probed with anti-human IgG alkaline phosphatase immunoconjugate (IgG-AP). (B) Western blot using pyrogenic IGIV-C containing Donor X plasma isolates as primary antibody and anti-human IgG-AP. (C) Western blot using non-pyrogenic IGIV-C as primary antibody and anti-human IgG-AP. (D) Instant Blue stained gel.

DETAILED DESCRIPTION

Figure 7:
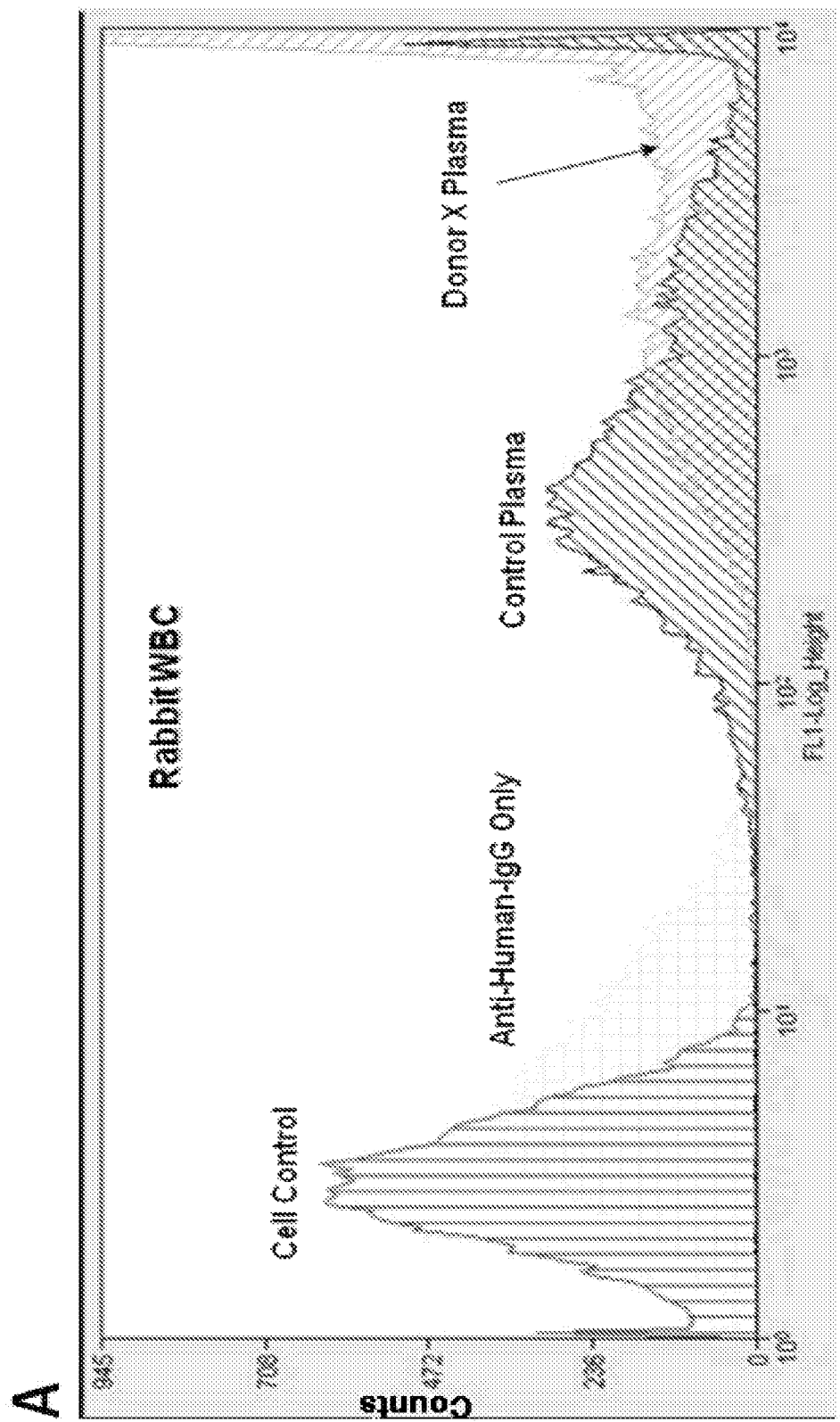
FIG. 7: Fluorescence Flow Cytometry Histograms. Rabbit WBCs were incubated with Donor X or control plasma, reacted with fluorescein-labeled anti-human IgG, and then analyzed by flow cytometry. Histograms show the relative fluorescence observed. Panels A and B show two separate experiments. Donor X plasma gave the largest signal with a relative fluorescence at least three times that of the control plasma. See Tables 4 and 5 for quantitative results.
Figure 7:
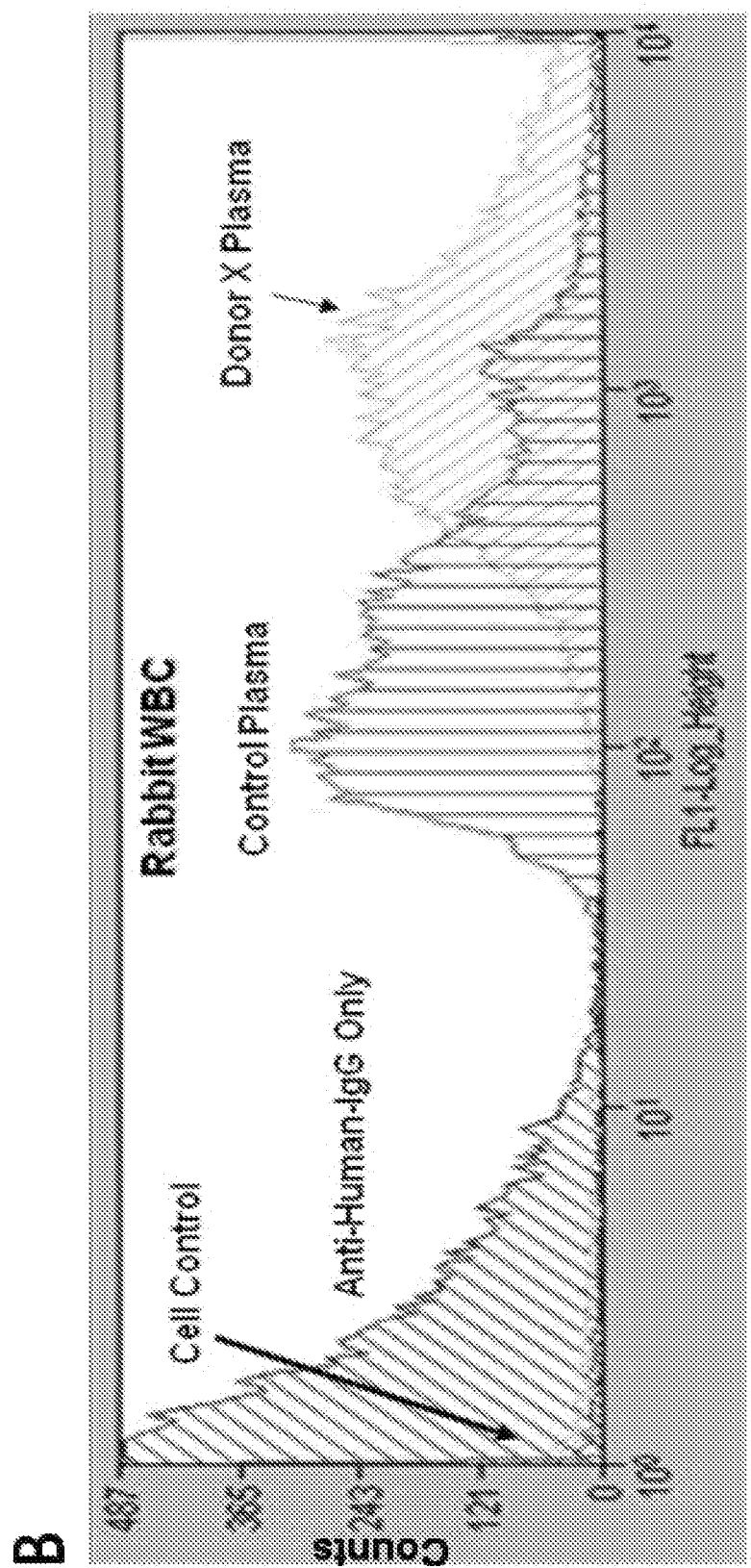

Described herein are methods for identifying atypical antibodies in blood and blood products. An individual, referred to herein as "Donor X," donated plasma that was pooled with other units for the manufacture of biotherapeutic protein products. During processing, the pooled plasma was assayed for pyrogenicity using the USP pyrogenicity rabbit assay. Unexpectedly, the pooled plasma tested positive as pyrogenic in the USP rabbit test. Further assays traced the pyrogenic agent to Donor X's plasma. Limulus amebocyte lysate (LAL) assays showed that Donor X plasma was not contaminated with bacterial endotoxins. Instead, the assays described herein demonstrated that Donor X's plasma contained atypical antibodies that were responsible for the pyrogenic response. Specifically, light and fluorescence microscopic examinations showed that Donor X plasma agglutinated rabbit and rat WBCs but not human WBCs. The rabbit WBC cross-reactivity was specific to Donor X because plasma from Donor X's parents, siblings, and children did not react. Fluorescent flow cytometry experiments showed that Donor X plasma contained IgG antibodies reactive with rabbit WBC cell-surface antigens and Western blot experiments confirmed the reactivity of the IgGs with rabbit sera. Collectively, these results suggest that Donor X may have been exposed to rodents or insect vectors of rodents that could have induced humoral immunity cross-reactive with rabbit WBCs. Thus, plasma from some individuals can test positive in USP rabbit pyrogen tests, not because they are contaminated with bacteria, but because they contain atypical antibodies that are cross-reactive with rabbit WBC antigens.

EXAMPLES

Example 1

United States Pharmacopia (USP) Pyrogen Assays

The current United States Pharmacopia §151 outlines the pyrogen assay. The test involves measuring the rise in temperature of rabbits following the intravenous injection of a test solution. This assay is designed to determine whether products can be tolerated by the test rabbit in a dose not to exceed 10 mL per kg injected intravenously within a period of not more than 10 minutes. Initially, three rabbits are injected. If any rabbit shows an individual temperature rise ≥0.5° C., the test is continued using five additional rabbits. If three or more of the eight rabbits show individual rises in temperature of ≥0.5° C. and/or the sum of the eight individual temperature rises exceeds 3.3° C. the material under examination is considered pyrogenic.

A sample of Donor X plasma or a pooled sample without any Donor X plasma was diluted 1:100 into 10 mL of sodium chloride solution (0.9% NaCl) and injected into the ear veins of three healthy mature rabbits. The rabbits' temperatures were measured rectally within 10 minutes of injection. Temperature data are shown in Table 1. The Donor X-free plasma sample did not induce a temperature increase in any of the rabbits. In contrast, when Donor X plasma was tested, temperature increases of between 1.1-1.2° C. were measured. Since the total temperature increase for the 3 rabbits was 3.4° C., Donor X plasma was considered pyrogenic and there was no need to extend testing to another 5 rabbits.

The immunoglobulins in a Pool containing 0% or 10% Donor X plasma were captured using a protein A column and tested for pyrogenicity. The Donor X-free plasma sample did not induce an increase in temperature but samples containing Donor X plasma were highly pyrogenic. These results indicated that the pyrogenic response in rabbits could be related to immunoglobulins in Donor X plasma.

TABLE 1

Donor X plasma causes pyrogenic responses in rabbits

| Sample | USP Pyrogen Max Temp Increase (° C.) | | | |
|---|---|---|---|---|
| | Rabbit 1 | Rabbit 2 | Rabbit 3 | Total ΔT |
| Plasma Donor X (1:100) | 1.1 | 1.1 | 1.2 | 3.4 |
| Pooled Plasma w/o Donor X (1:100) | 0.0 | 0.0 | 0.0 | 0.0 |
| Pooled Mab Eluate w/ 10% Donor X | 2.0 | 2.4 | 1.6 | 6.0 |
| Pooled Mab Eluate w/o Donor X | 0.0 | 0.1 | 0.0 | 0.1 |

Example 2

A series of experiments were performed using Donor X plasma to better understand the nature of its pyrogenicity.

White Blood Cell Agglutination and Microscopy Experiments

Agglutination experiments were performed to evaluate interactions between Donor X plasma and rabbit or human white blood cells (WBC). WBCs were harvested from rabbit and human whole blood by density gradient centrifugation using Histopaque® (Sigma-Aldrich) and suspended in normal buffered saline supplemented with BSA. The rabbit and human WBCs were then incubated with Donor X and control plasma in a 96-well microplate. Following incubation and washing, fluorescent-labeled anti-human IgG was added, and microplates were incubated, washed, and examined microscopically. Each well was examined for agglutination using visible light and phase contrast microscopy, and then viewed using fluorescence microscopy (results discussed in the subsequent section).

Significant agglutination was observed in test wells containing Donor X plasma and rabbit WBCs (FIGS. 1A and 1C) but not in test wells containing Donor X plasma and human WBCs (FIGS. 2A and 2C). No agglutination was observed in wells containing control plasma and rabbit WBCs (FIGS. 1B and 1D) or control plasma and human WBCs (FIGS. 2B and 2D). These results were reproduced in numerous assays and indicate that Donor X IgG binds to rabbit WBCs, but not to human WBCs. See FIG. 2.

During several of the agglutination experiments, cytotoxicity was observed in samples containing rabbit WBCs and Donor X plasma but not in wells containing control plasma and rabbit WBCs, nor any wells containing human WBCs with Donor X or control plasma. The observation that Donor X plasma is toxic to rabbit WBCs suggested specific binding of Donor X immunoglobulins to these cells. See FIGS. 1-3.

Fluorescent Microscopy Experiments

Fluorescent microscopy experiments were performed in parallel with the agglutination and light microscopy studies described above and the results are presented in Table 2. Rabbit WBCs were strongly fluorescent in samples incubated with Donor X plasma (FIGS. 4A and 5A), compared to a relatively weak degree of fluorescence for samples incubated with control plasma (FIG. 4B) or with only fluorescent-labeled anti-human IgG. See FIGS. 4 and 5. These findings indicated that the fluorescence observed for rabbit WBCs was specific to IgG present in Donor X. A weak degree of fluorescence was observed for human WBCs incubated with both Donor X and control plasma (FIG. 6) or with only the fluorescent-labeled anti-human IgG (no Donor X or control plasma added). FIG. 6B. These findings indicated that the fluorescence observed with human WBCs represented non-specific binding, independent of the presence of Donor X or control IgG.

TABLE 2

Fluorescent Microscopy Results

| Plasma Source | Host WBC | Fluorescent-labeled anti-human IgG | Fluorescence Score (0-4) |
|---|---|---|---|
| Donor X | Rabbit | Yes | 3-4 |
| Control | Rabbit | Yes | 0-2 |
| None | Rabbit | Yes | 0-1 |
| Donor X | Human | Yes | 0-1 |
| Control | Human | Yes | 0-1 |
| None | Human | yes | 0-1 |

Example 3

Flow Cytometry Experiments

In order to quantitate antibody binding and the fluorescence observed by microscopy, flow cytometry studies were performed. In these experiments, rabbit and human WBCs were incubated with Donor X and control plasma and washed before adding and incubating with fluorescent-labeled anti-human IgG. The cell samples were washed, resuspended in normal buffered saline to a concentration ranging from approximately $3 \times 10^6$ to $5 \times 10^6$ cells/mL and analyzed by flow cytometry.

FIG. 7 contains histogram overlays showing relative fluorescent intensity of two different rabbit WBC samples incubated with Donor X or control plasma. Two additional samples were included as assay controls, unstained rabbit WBCs (cell control) and rabbit WBCs treated with fluorescent-labeled anti-human-IgG only. The median fluorescence of the rabbit WBC sample incubated with Donor X plasma was 3264 in experiment 1 and 922 in experiment 2 and, significantly higher than that observed after incubating rabbit WBCs with control plasma (median fluorescence of 499 and 175 for experiments 1 and 2, respectively). See Tables 3 and 4. Thus, even though there was some overlap between the rabbit WBCs incubated with Donor X and control plasma, there was a distinct difference in fluorescent intensity. These results correlated well with the microscopy study results, discussed above, where WBCs reacted with Donor X plasma and produced significantly stronger fluorescence that those incubated with control plasma.

TABLE 3

Flow cytometry histogram data showing relative fluorescence of rabbit WBCs incubated with Donor X or control plasma

| Experiment 1 Cell Type | Relative Fluorescence (N = 20,0000) | | | | |
|---|---|---|---|---|---|
| | Mean | Median | Mode | Mode Count | Std Dev |
| Donor X Plasma | 4,507.4 | 3,263.8 | 10,000.1 | 1,632 | 3,688.4 |
| Control Plasma | 1,508.9 | 498.9 | 9,003.1 | 509 | 2,404.3 |
| Anti-IgG only | 13.4 | 5.7 | 3.7 | 400 | 176.3 |
| Cell Control | 4.3 | 3.0 | 3.4 | 630 | 49.7 |

TABLE 4

Flow cytometry histogram data showing relative fluorescence of rabbit WBCs incubated with Donor X or control plasma

| Experiment 2 Cell Type | Relative Fluorescence (N = 20,0000) | |
|---|---|---|
| | Mean | Median |
| Donor X Plasma | 1752 | 922 |
| Control Plasma | 501 | 175 |
| Anti-IgG only | 13 | 1 |
| Cell Control | 1 | 1 |

Figure 8:
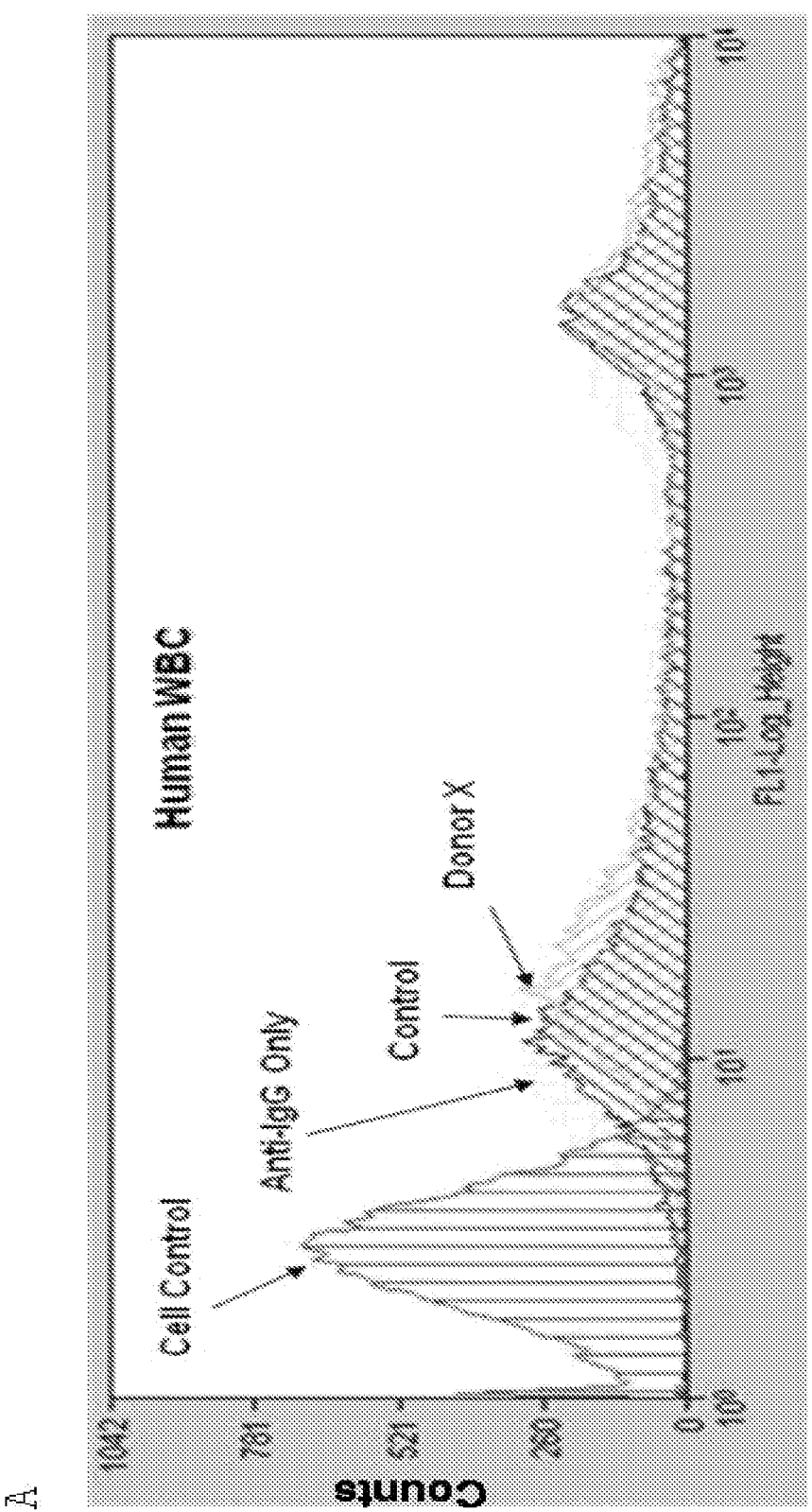
FIG. 8: Fluorescence Flow Cytometry Histograms. Human WBCs were incubated with Donor X or control plasma, reacted with fluorescein-labeled anti-human IgG, and then analyzed by flow cytometry. Histograms show the relative fluorescence observed. Panels A and B show two separate experiments. Donor X plasma was not significantly different from the control plasma. See Tables 6 and 7 for quantitative results.
Figure 8:
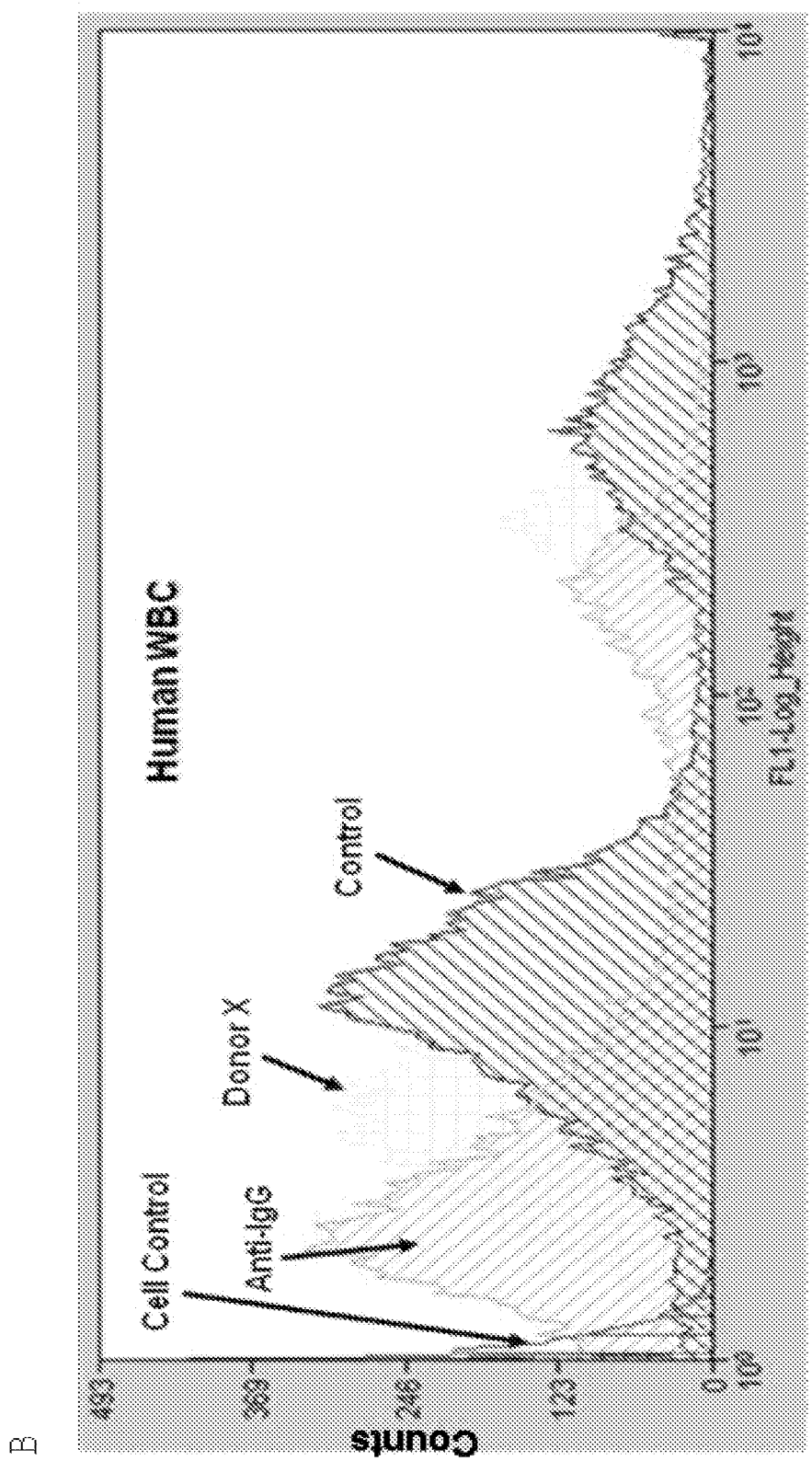

The flow cytometry experiments were repeated with human WBCs and the results are shown in FIG. 8 and Tables 5 and 6. Human WBCs incubated with Donor X plasma and control plasma had similar histograms, indicating no significant difference in fluorescent intensity. These results correlated with microscopy study results, discussed previously, in which human WBCs treated with Donor X and control plasma produced a similar degree of fluorescence. The human WBC sample stained with only fluorochrome-labeled anti-human-IgG also showed significant overlap with Donor X and control plasma samples, and thus indicated a significant degree of non-specific binding by the secondary antibody.

TABLE 5

Flow cytometry histogram data showing relative fluorescence of human WBCs incubated with Donor X or control plasma

| Experiment 3 Cell Type | Relative Fluorescence (N = 20,0000) | | | | |
|---|---|---|---|---|---|
| | Mean | Median | Mode | Mode Count | Std Dev |
| Donor X Plasma | 1004.9 | 47.7 | 16.1 | 304 | 1739.0 |
| Control Plasma | 820.9 | 37.0 | 11.3 | 294 | 1472.1 |
| Anti-IgG only | 381.8 | 17.4 | 9.4 | 332 | 785.5 |
| Cell Control | 5.6 | 2.8 | 2.9 | 695 | 2663.1 |

TABLE 6

Flow cytometry histogram data showing relative fluorescence of human WBCs incubated with Donor X or control plasma

| Experiment 4 Cell Type | Relative Fluorescence (N = 20,0000) | |
|---|---|---|
| | Mean | Median |
| Donor X Plasma | 174 | 7 |
| Control Plasma | 274 | 16 |
| Anti-IgG only | 76 | 4 |
| Cell Control | 1 | 1 |

In summary, the flow cytometry analyses showed significant binding of Donor X immunoglobulins (i.e., IgGs) to rabbit WBCs as compared to control plasma and minimal binding to human WBCs.

Example 4

Supplemental Rabbit Pyrogen Testing

In order to evaluate a possible genetic association for Donor X immunoglobulins and their effect on rabbit pyrogenicity, USP pyrogen assays were performed on sera donated by relatives of Donor X. A sample of Donor X serum was also tested as a control. Because previous studies demonstrated that Donor X plasma produced a significant pyrogen response at dilutions of 1:100, all test samples were diluted 1:100 in sterile normal saline (0.9% NaCl, USP, for injection) prior to rabbit pyrogen testing. An aliquot of each sample was also used in a LAL assay to examine endotoxin contamination as a source of pyrogen response. Pyrogen and LAL results are presented in Table 7.

TABLE 7

USP Pyrogen Test Results for Donor X and Immediate Family Members

| Sera Samples (1:100 dilution) | USP Rabbit Pyrogen Results (max. temperature increase in ° C.) | | | |
|---|---|---|---|---|
| | Rabbit 1 | Rabbit 2 | Rabbit 3 | Total ΔT |
| Donor X | 1.0 | 0.3 | 0.6 | 1.9 |
| Father | 0.0 | 0.1 | 0.0 | 0.1 |
| Mother | 0.0 | 0.2 | 0.0 | 0.2 |
| Sister 1 | 0.0 | 0.0 | 0.0 | 0.0 |
| Brother | 0.0 | 0.0 | 0.0 | 0.0 |

TABLE 7-continued

USP Pyrogen Test Results for Donor
X and Immediate Family Members

| Sera Samples (1:100 dilution) | USP Rabbit Pyrogen Results (max. temperature increase in ° C.) | | | |
|---|---|---|---|---|
| | Rabbit 1 | Rabbit 2 | Rabbit 3 | Total ΔT |
| Sister 2 | 0.0 | 0.1 | 0.0 | 0.1 |
| Daughter 1 | 0.0 | 0.1 | 0.1 | 0.2 |
| Daughter 2 | 0.0 | 0.2 | 0.0 | 0.2 |
| Son | 0.0 | 0.1 | 0.0 | 0.1 |

Serum from Donor X produced a significant temperature increase in two of the three test rabbits, with a total temperature increase of 1.9° C. This response was consistent with previous testing with Donor X plasma. Serum from Donor X's relatives, including parents, siblings, and children produced no significant temperature increases. Limulus Amoebocyte Lysate assay (LAL) results for all samples were negative, indicating that exogenous endotoxin did not contribute to the rabbit pyrogenic responses.

Example 5

Red Blood Cell Agglutination Studies

Donor X plasma was tested with rabbit red blood cells in a series of agglutination experiments to determine if Donor X plasma contains immunoglobulins specific for antigens on rabbit RBCs. Incompatibility between Donor X plasma immunoglobulins and rabbit RBCs could potentially cause hemolysis and pyrogenicity. For these studies, Donor X and control plasma were titrated against a suspension of rabbit RBCs. The suspension was observed at three time points: (1) immediately; (2) after a 30-minute incubation at 37° C.; and (3) after anti-human-globulin serum was added.

Both Donor X and control plasma produced strong agglutination of rabbit RBCs at all time points, and an equivalent titer was observed for Donor X and the positive control. Hemolysis was observed at low dilutions of both Donor X and the positive control.

The presence of anti-A, and/or anti-B immunoglobulins present in Donor X and control plasma could potentially cross-react with rabbit RBC antigens with similar epitopes to human A and B antigens. Accordingly, Donor X and control plasma were pre-absorbed with human A and/or B RBCs to remove cross-reacting anti-A and anti-B antibodies. The pre-absorbed plasma was then tested against rabbit RBCs as described above. Both Donor X and control plasma produced strong agglutination, similar to the initial results. No difference in reactivity was observed between Donor X and the control plasma. These results showed the presence of antibodies in Donor X plasma with broad cross-reactivity to antigens/epitopes on rabbit RBCs. In addition, these results suggest that an RBC-mediated process is not responsible for the pyrogenic response in rabbits.

Donor X plasma was also tested for antibodies to human RBC antigens using a RBC antibody-identification panel. Negative results were obtained with all panel cells, confirming that Donor X plasma contains no clinically significant alloantibodies.

Antigen phenotyping was also performed on Donor X RBCs, included typing for RBC antigens belonging to the Rh, Kell, Duffy, Kidd, Lewis, MNS, P, and Lutheran blood group systems. Donor X RBCs were of a common RBC phenotype, and there were no unusual results.

Example 6

Downstream plasma products containing Donor X plasma were assayed to identify the factor responsible for generating the pyrogenic-response. Human Immunoglobulin Globulin, Intravenous containing 10% caprylate/chromatography purified (e.g., IGIV-C 10%, i.e., Gamunex®, Grifols Therapeutics Inc., formerly Talecris Biotherapeutics, Inc.) that was produced from plasma pools containing Donor X plasma was assayed using Western blotting.

Western Blotting

Figure 9:
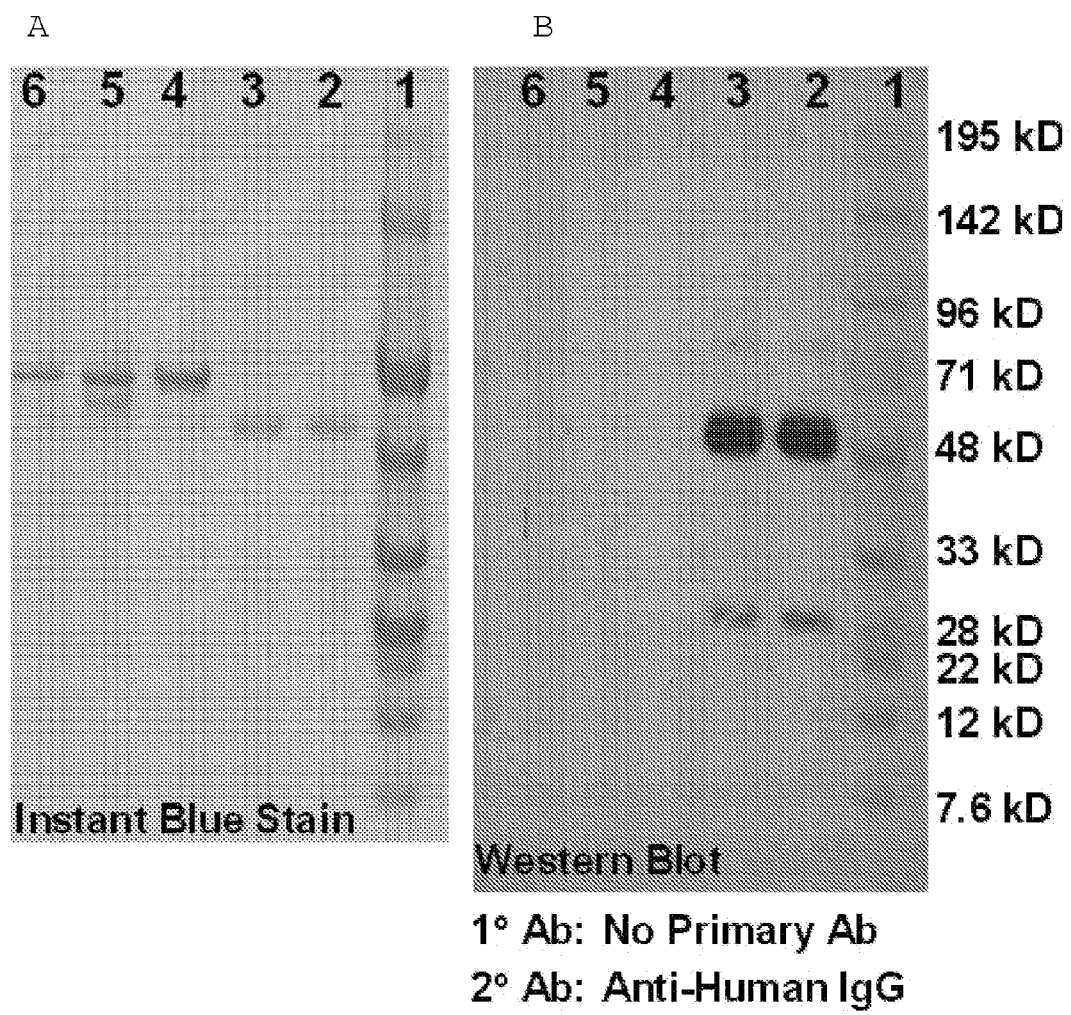
FIG. 9: Electrophoresis and Western Blotting Analysis of Samples of Pyrogenic IVIG-C Containing Donor X Plasma Isolates. Lane 1: MW markers; Lane 2: Pyrogenic IGIV-C (Donor X); Lane 3: Non-pyrogenic IGIV-C; Lane 4: Rabbit Serum; Lane 5: Fetal Bovine Serum; Lane 6: Horse Serum. (A) Instant Blue stained gel. (B) Western blot control (no primary antibody) probed with anti-human IgG alkaline phosphatase immunoconjugate (IgG-AP). (C) Western blot using pyrogenic IGIV-C containing Donor X plasma isolates as primary antibody and anti-human IgG-AP. (D) Western blot using non-pyrogenic IGIV-C as primary antibody and anti-human IgG-AP.
Figure 9:
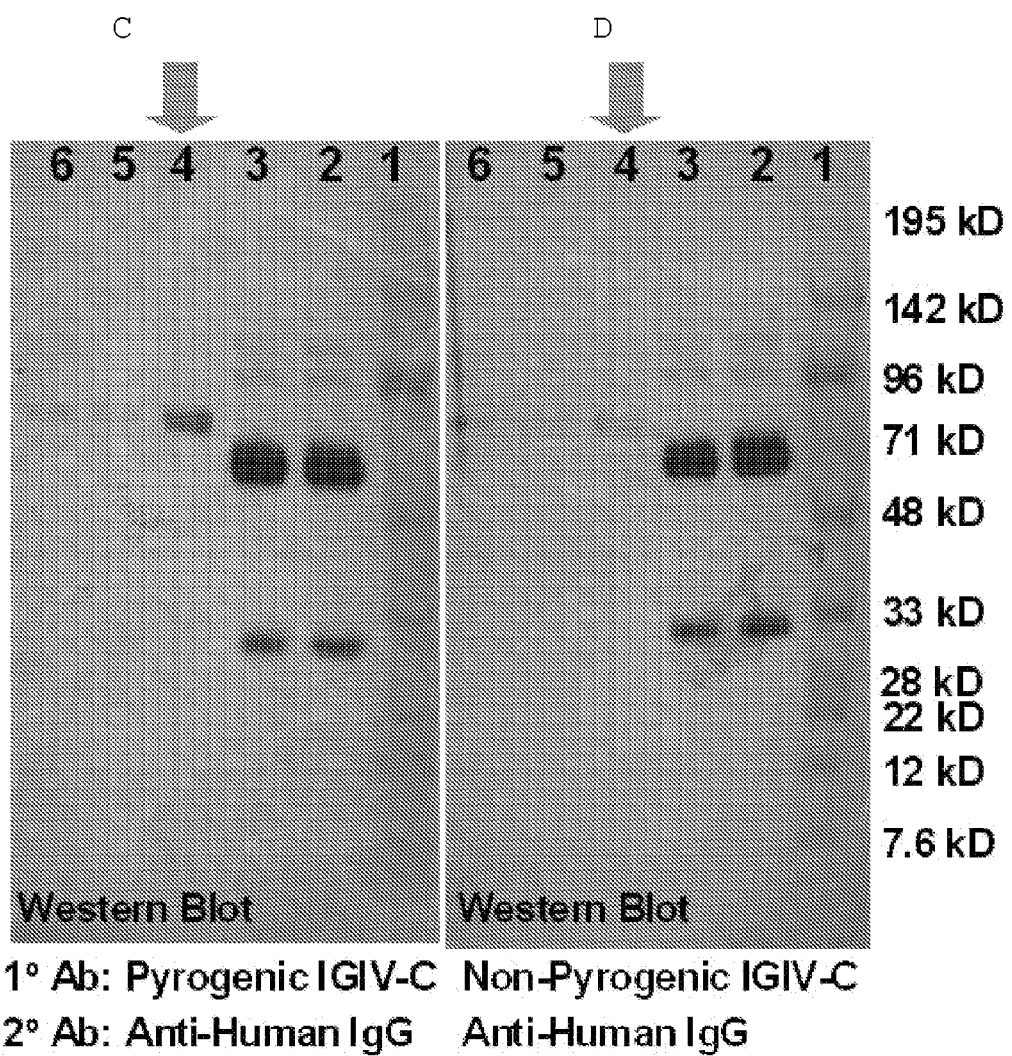

Samples of "pyrogenic" IGIV-C produced from Donor X-containing plasma pools , non-pyrogenic IGIV-C produced from Donor X-free plasma pools, rabbit serum, fetal bovine serum, and horse serum were run on four 4-20% reducing SDS-PAGE gels. One gel was stained with Instant Blue (FIG. 9A) while the other three were transferred to PVDF membranes (FIGS. 9B-D). One membrane was reacted with only anti-Human IgG conjugated to alkaline phosphatase (FIG. 9B). The remaining membranes were reacted with pyrogenic IGIV-C or with non-pyrogenic IGIV-C, and then with the anti-Human IgG alkaline phosphatase conjugate (FIGS. 9C-D). Lane 1: MW markers; Lane 2: Pyrogenic IGIV-C (Donor X); Lane 3: Non-pyrogenic IGIV-C; Lane 4: Rabbit Serum; Lane 5: Fetal Bovine Serum; Lane 6: Horse Serum.

The Instant Blue-stained gel showed that comparable amounts of rabbit serum, fetal bovine serum and horse serum were loaded on the gel. Lanes 4-6 in FIG. 9A. The membrane stained with only anti-Human IgG showed that the secondary antibody (anti-human IgG) was specific and reacted only with human IgG (pyrogenic and non-pyrogenic IGIV-C). Lanes 2 and 3 in FIG. 9B. The membrane reacted with pyrogenic IGIV-C and the anti-Human IgG alkaline phosphatase conjugate showed that pyrogenic IGIV-C reacted strongly to rabbit serum and weakly with fetal bovine and horse serum. Lanes 4-6 in FIG. 9C. The membrane reacted with non-pyrogenic IGIV-C and the anti-Human IgG alkaline phosphatase conjugate showed that non-pyrogenic IGIV-C reacted weakly with the three test serums, including rabbit serum. Lanes 4-6 in FIG. 9D. Collectively, these results indicate that pyrogenic IGIV-C reacts strongly with rabbit sera, while non-pyrogenic IGIV-C does not.

Samples of fetal bovine serum and various concentrations of rabbit serum were run on four 4-20% SDS-PAGE gels. Three gels were transferred to PVDF membranes (FIGS. 10A-C), and one gel was stained with Instant Blue (FIG. 10D). One membrane was reacted with only anti-Human IgG conjugated to alkaline phosphatase (FIG. 10A). The remaining membranes were reacted with pyrogenic IGIV-C or with non-pyrogenic IGIV-C, and then with the anti-Human IgG alkaline phosphatase immunoconjugate (FIGS. 10B-C). Lane 1: MW markers; Lane 2: Fetal Bovine Serum; Lane 3: Rabbit Serum; Lane 4: Rabbit Serum, diluted 1:5; Lane 5: Rabbit Serum, diluted 1:10; Lane 6: Rabbit Serum, diluted 1:50.

The Western blot was negative when the membrane was probed with only anti-Human IgG. FIG. 10A. However, when pyrogenic IGIV-C was used as the primary Ab, it specifically reacted to undiluted rabbit serum and rabbit serum diluted 1:5 and 1:10. See Lanes 3-5 in FIG. 10B. The 1:50 dilution of rabbit serum was not reactive (Lane 6). Only undiluted rabbit serum was detected when non-pyrogenic IGIV-C was used as the primary antibody. Lane 4 in FIG. 10C. The Instant Blue-stained gel showed the relative amounts of fetal bovine serum and rabbit serum that were loaded onto the gels. Lanes 2-3 in FIG. 10D. Overall, these results indicate that pyrogenic IGIV-C contains ~10-fold more antibodies against rabbit serum than non-pyrogenic IGIV-C.

Example 7

Rat WBC Fluorescence Microscopy and Agglutination

Figure 11:
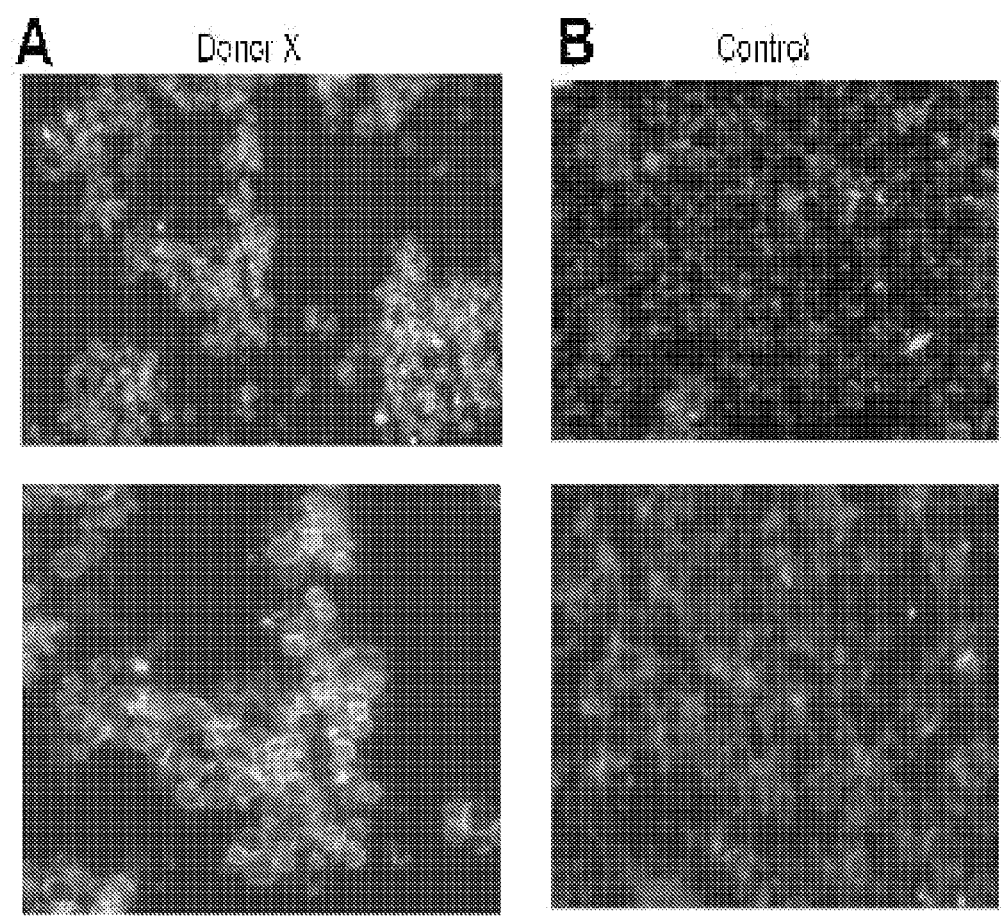
FIG. 11: Donor X's Plasma Cross-reacts with Rat WBCs: Fluorescence Microscopy of Rat WBC Agglutination Assays. Rat WBCs were incubated with Donor X or control plasma, reacted with fluorescein-labeled anti-human IgG, and then viewed using fluorescence microscopy. Panel (A) shows positive fluorescence and agglutination of rat WBCs incubated with fluorescein-labeled anti-human IgG and a 40× image of the agglutinated cells (bottom panel). These results indicate that Donor X's plasma contains IgGs reactive with rat WBC cell-surface antigens. Panel (B) shows the weak fluorescence observed with the control plasma and a 40× image of the rat WBCs showing no agglutination (bottom panel).

Rat WBCs were isolated from whole blood by density gradient centrifugation using Histopaque®. Rat WBCs were reacted with Donor X plasma as described for Example 2 above. Donor X plasma produced distinct agglutination and fluorescence with Rat WBCs. See FIG. 11.

Example 8

Summary of Results

The results of the microscopy (FIGS. 1-6) and flow cytometry experiments (FIGS. 7-8) indicated that Donor X IgG readily bound to rabbit WBCs. Antibody-binding was demonstrated by both agglutination and fluorescent intensity. Although control plasma produced some fluorescence with rabbit WBCs, the degree of fluorescence was significantly less than that observed with Donor X. Control plasma did not cause agglutination of rabbit WBCs in any of the experiments, while Donor X plasma consistently produced agglutination. Donor X plasma (IgG) did not produce agglutination with human WBCs in any of the experiments, indicating that Donor X IgG did not bind to human WBCs.

The binding of Donor X IgG to rabbit WBCs is a likely trigger for rabbit WBC activation and release of endogenous (leukocytic) pyrogens, which caused the observed fever response.

Rabbit pyrogen assays conducted on immediate family of Donor X (i.e., parents, siblings, and children) were uniformly negative. Table 7. These results indicated that the unique properties of Donor X IgG, with regard to rabbit temperature response, were not dominant allele-based, but rather antibody-specific to Donor X.

Experiments with rabbit RBCs demonstrated that both Donor X and control plasma contained antibodies with broad cross-reactivity to an antigen on rabbit RBCs. Donor X and control plasma produced very similar reactions with rabbit RBCs, suggesting that an RBC-mediated process is not responsible for the pyrogenic response in rabbits.

Western Blotting experiments showed that that pyrogenic IGIV-C (containing Donor X plasma isolates) reacts strongly with rabbit sera, while non-pyrogenic IGIV-C does not. This indicates that the presence of atypical IgGs from Donor X in the pyrogenic IGIV-C, were responsible for eliciting a pyrogenic response in the USP pyrogen test. In addition, the Western Blotting experiments showed that pyrogenic IGIV-C contains ~10-fold more antibodies against rabbit serum than non-pyrogenic IGIV-C. This indicated a probable stiochastic effect from the Donor X atypical antibodies that caused pyrogenic responses.

Experiments with rat white blood cells show that Donor X plasma is capable of cross reacting with and causing agglutination of rat WBCs. These results suggested that direct exposure to rats or indirect exposure by insect vectors of rodents (e.g., fleas), might have lead to "atypical" IgG-immunoglobulin immunity with cross-reactivity to both rat and rabbit cells.

Example 9

High-Throughput Assays

High-throughput ELISA, fluorescence, or Western blot experiments are be performed by incubating test samples in 96-well, 192-well, or 384-well plates or membranes, washing, blocking, and probing the samples using enzyme- or fluorophore-immunoconjugates and then analyzing the results via fluorometry, luminometry, densitometry, colorimetry, or UV/visible absorbance, among other detection methods. Such high-throughput assays permit in-line analysis of blood or plasma samples or products before, during, and after processing and can eliminate reactive samples, such as those containing atypical immunoglobulins, which may produce false-positive pyrogen results in assays.

What is claimed is:

1. A method for identifying atypical reactive antibodies for a blood products manufacturing process, the method comprising:
   (a) obtaining a sample of blood or plasma from each of a plurality of blood or plasma units, said sample suspected of containing the atypical reactive antibodies;
   (b) testing each of the samples and a control sample known not to contain atypical reactive antibodies using any one or more assays selected from the group consisting of cellular agglutination, fluorescence microscopy, immunoprecipitation assay, immunodiffusion assay, immunofluorescence, ELISA, flow cytometry, FACS, and Western blotting for binding of components of the sample to antigens in rabbit serum or blood cells, said components comprising the atypical reactive antibodies if present in the sample and other factors capable of non-specific binding to the antigens in the rabbit serum or blood cells;
   (c) comparing results obtained from said assay between the tested samples and the control sample;
   (d) determining whether each of the tested samples contain reactive atypical antibodies by determining increased binding of the components of the tested sample to the antigens in the rabbit serum or blood cells relative to the non-specific binding of the other factors contained in components of the control sample to the rabbit serum or blood cells, wherein, if the increased binding is determined from the tested sample as compared to the non-specific binding from the control sample, the components of the tested sample that bind to the rabbit serum or blood cells comprises the atypical antibodies;
   (e) pooling the plurality of blood or plasma units that were the source of each of the tested samples that were determined not to contain reactive atypical antibodies while interdicting any blood or plasma unit from the pool that was the source of the tested sample if the tested sample was identified as containing reactive atypical antibodies in (d);
   (f) conducting a pyrogen assay on the pooled blood or plasma units, wherein said pyrogen assay comprises:
      (i) measuring a body temperature of a test rabbit;
      (ii) administering part of the pooled blood or plasma units to the test rabbit;
      (iii) measuring a body temperature of the test rabbit after the administration; and
      (iv) determining if the body temperature of the test rabbit rises >0.5° C. from before to after administration; and (g) approving use of rest of the pooled blood or plasma units for the blood products manufacturing process if the body temperature of the test rabbit does not rise >0.5° C.

2. The method according to claim 1, wherein step (b) comprises a cellular agglutination assay.

3. The method according to claim 1, wherein step (b) comprises flow cytometry.

4. The method according to claim 1, wherein step (b) comprises Western blotting.

5. A method for manufacturing blood products, the method comprising:
- (a)-(g) identifying atypical reactive antibodies for the blood products manufacturing process according to claim 1; and
- (h) further processing the approved pooled blood or plasma units so as to provide said blood products.

* * * * *